US00PP20191P2

(12) United States Plant Patent
Miyazaki

(10) Patent No.: US PP20,191 P2
(45) Date of Patent: Jul. 28, 2009

(54) ***SENECIO* PLANT NAMED 'SUNSENELIBUBI'**

(50) Latin Name: ***Senecio cruentus*×*Senecio heritieri***
Varietal Denomination: Sunsenelibubi

(75) Inventor: Kiyoshi Miyazaki, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/157,319

(22) Filed: Jun. 9, 2008

(51) Int. Cl.
*A01H 5/00* (2006.01)

(52) U.S. Cl. ..... Plt./480

(58) Field of Classification Search ..... Plt./480
See application file for complete search history.

*Primary Examiner*—Annette H Para
(74) *Attorney, Agent, or Firm*—C. A. Whealy

(57) ABSTRACT

A new and distinct cultivar of *Senecio* plant named 'Sunsenelibubi', characterized by its compact, upright and mounded plant habit; freely branching growth habit; relatively small leaves; freely flowering habit; relatively long flowering period; and large daisy-type inflorescences with violet and white bi-colored ray florets and violet blue-colored disc florets.

1 Drawing Sheet

Botanical designation: *Senecio cruentus*×*Senecio heritieri.*

Cultivar denomination: 'SUNSENELIBUBI'.

Cross-referenced to related applications: Title: *Senecio* Plant Named 'Sunseneribuba'. Applicant: Kiyoshi Miyazaki. Filed: Concurrently with this application.

BACKGROUND OF THE INVENTION

The present invention relates to a new and distinct cultivar of *Senecio* plant, botanically known as *Senecio cruentus*× *Senecio heritieri,* and hereinafter referred to by the name 'Sunsenelibubi'.

The new *Senecio* is a product of a planned breeding program conducted by the Inventor in Hokuto-shi, Yamanashi, Japan. The objective of the program is to create and develop new *Senecio* cultivars with uniformly mounded plant habit, freely flowering habit and attractive inflorescence coloration.

The new *Senecio* originated from a cross-pollination by the Inventor in January, 1995 of a proprietary selection of *Senecio cruentus* identified as code number BW20, not patented, as the female, or seed, parent with a proprietary selection of *Senecio heritieri* identified as code number E-21, not patented, as the male, or pollen, parent. The new *Senecio* was discovered and selected by the Inventor as a single flowering plant within the progeny of the stated cross-pollination in a controlled greenhouse environment in Hokuto-shi, Yamanashi, Japan.

Asexual reproduction of the new *Senecio* by terminal cuttings in a controlled greenhouse environment in Higashiomi, Shiga, Japan since March, 2004, has shown that the unique features of this new *Senecio* are stable and reproduced true to type in successive generations.

SUMMARY OF THE INVENTION

Plants of the new *Senecio* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunsenelibubi'. These characteristics in combination distinguish 'Sunsenelibubi' as a new and distinct cultivar of *Senecio*:

1. Compact, upright and mounded plant habit.
2. Freely branching growth habit.
3. Relatively small leaves.
4. Freely flowering habit.
5. Relatively long flowering period.
6. Large daisy-type inflorescences with violet and white bi-colored ray florets and violet blue-colored disc florets.

Plants of the new *Senecio* differ from plants of the female parent selection in the following characteristics:

1. Plants of the new *Senecio* are taller than plants of the female parent selection.
2. Plants of the new *Senecio* have smaller leaves than plants of the female parent selection.

Plants of the new *Senecio* differ from plants of the male parent selection in the following characteristics:

1. Plants of the new *Senecio* have larger leaves than plants of the male parent selection.
2. Plants of the new *Senecio* and the male parent selection differ in ray florets color as plants of the male parent selection have solid violet blue-colored ray florets.

Plants of the new *Senecio* differ from plants of *Senecio cruentus*×*Senecio heritieri* 'Sunseneribuba' primarily in ray floret color as plants of the new *Senecio* have lighter-colored ray florets than plants of 'Sunseneribuba'.

Plants of the new *Senecio* can also be compared to plants of *Senecio* 'Jupiter Blue-White', not patented. In side-by-side comparisons conducted in Higashiomi, Shiga, Japan, plants of the new *Senecio* differed from plants of 'Jupiter Blue-White' in the following characteristics:

1. Plants of the new *Senecio* were taller and had longer internodes than plants of 'Jupiter Blue-White'.
2. Plants of the new *Senecio* were more freely branching than plants of 'Jupiter Blue-White'.

3. Plants of the new *Senecio* had smaller leaves than plants of 'Jupiter Blue-White'.
4. Plants of the new *Senecio* flower earlier than plants of 'Jupiter Blue-White'.
5. Plants of the new *Senecio* had larger inflorescences than plants of 'Jupiter Blue-White'.
6. Plants of the new *Senecio* had longer peduncles than plants of 'Jupiter Blue-White'.

BRIEF DESCRIPTION OF THE PHOTOGRAPHS

The accompanying photographs illustrate the overall appearance of the new *Senecio*. These photographs show the colors as true as it is reasonably possible to obtain in colored reproductions of this type. Colors in the photographs may differ slightly from the color values cited in the detailed botanical description which accurately describe the colors of the new *Senecio*.

The photograph at the top of the sheet comprises a side perspective view of a typical flowering plant of 'Sunsenelibubi' grown in a container.

The photograph at the bottom of the sheet is a close-up view of a typical inflorescence and inflorescence buds of 'Sunsenelibubi'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown in Higashiomi, Shiga, Japan during the winter in a polyethylene-covered greenhouse and under conditions and practices which approximate those generally used in commercial *Senecio* production. During the production of the plants, day temperatures averaged 20° C. and night temperatures averaged 10° C. Measurements and numerical values represent averages for typical flowering plants. Plants were six month old when the photographs and description were taken.

Botanical classification: *Senecio cruentus*×*Senecio heritieri* 'Sunsenelibubi'.

Parentage:

*Female, or seed, parent.*—Proprietary selection of *Senecio cruentus* identified as code number BW20, not patented.

*Male, or pollen, parent.*—Proprietary selection of *Senecio heritieri* identified as code number E-21, not patented.

Propagation:

*Type.*—Terminal vegetative cuttings.

*Time to initiate roots.*—About one week at 20° C.

*Time to produce a rooted cutting.*—About four weeks at 20° C.

*Root description.*—Fine, fibrous, fleshy; light brown in color.

*Rooting habit.*—Freely branching.

Plant description:

*Plant form/growth habit.*—Compact, upright and mounded plant habit. Inflorescences positioned well above the foliar plane. Vigorous growth habit.

*Plant height.*—About 30 cm.

*Plant diameter.*—About 31.2 cm.

*Lateral branches.*—Quantity per plant: Freely branching, about 16 lateral branches per plant. Length: About 17 cm. Diameter: About 3.5 mm. Internode length: About 1.2 cm. Strength: Strong. Texture: Pubescent. Color: Close to 146C.

*Foliage description.*—Arrangement: Alternate, simple. Length: About 5.8 cm. Width: About 6 cm. Shape: Roughly cordate with shallow lobes. Apex: Obtuse to acute. Base: Cordate. Margin: Shallowly lobed; crenate; slightly undulate. Texture, upper surface: Sparsely pubescent. Texture, lower surface: Densely pubescent. Venation pattern: Pinnate; reticulate. Color: Developing and fully expanded foliage, upper surface: Close to 137B; venation, close to 144D. Developing and fully expanded foliage, lower surface: Close to 191B; venation, close to 144D. Petiole length: About 6.9 cm. Petiole diameter: About 2.2 mm. Petiole texture, upper and lower surfaces: Sparsely pubescent. Petiole color, upper and lower surfaces: Close to 144D.

Inflorescence description:

*Appearance.*—Daisy-type inflorescence form with elliptic-shaped ray florets. Inflorescences positioned above the foliage, arising from leaf axils. Disc and ray florets developing acropetally on a capitulum. Inflorescences face mostly upright. Freely flowering habit with about 15 inflorescences developing per plant. Inflorescences persistent.

*Fragrance.*—Faintly scented.

*Flowering response.*—In Higashiomi, Shiga, Japan, plants of the new *Senecio* flower continuously from winter to late spring. Inflorescences last about two weeks on the plant.

*Inflorescence bud.*—Height: About 7.8 mm. Diameter: About 7.2 mm. Shape: Globose. Color: Close to 144A.

*Inflorescence size.*—Diameter: About 7.3 cm. Depth (height): About 1.3 cm. Disc diameter: About 1.1 cm.

*Ray florets.*—Shape: Elliptic. Length: About 3.1 cm. Width: About 1.1 cm. Apex: Truncate, rounded, emarginate or praemorse. Base: Obtuse. Margin: Entire. Texture, upper and lower surfaces: Smooth, glabrous; satiny. Number of ray florets per inflorescence: About 13 in a single whorl. Color: When opening, upper surface: Towards the apex, close to N88A; towards the base, close to 155C. When opening, lower surface: Close to 91D. Fully opened, upper surface: Towards the apex, close to N88B; towards the base, close to 155C. Towards the apex, color becoming closer to N87D with development. Fully opened, lower surface: Close to 91D.

*Disc florets.*—Shape: Tubular; apex dentate, five-pointed. Length: About 1 cm. Diameter: About 2.2 mm. Number of disc floret per inflorescence: About 140. Color, immature: Close to N89A. Color, mature: Close to N88A.

*Phyllaries.*—Quantity per inflorescence: About twelve in a single whorl. Length: About 7.8 mm. Width: About 2.5 mm. Shape: Lanceolate. Apex: Acute. Base: Fused. Margin: Entire. Texture, upper and lower surfaces: Smooth, glabrous. Color, upper and lower surfaces: Close to 144A.

*Peduncles.*—Length: About 5.3 cm. Diameter: About 1.6 mm. Strength: Strong. Aspect: Mostly upright. Texture: Smooth, glabrous. Color: Close to N186C.

*Reproductive organs.*—Androecium: Present on disc florets only. Anther shape: Ellipsoidal. Anther color:

Close to N88A. Pollen amount: Moderate. Pollen color: Close to 14B. Gynoecium: Present on both ray and disc florets. Stigma shape: Bi-parted. Stigma color: Close to N88A.

*Seeds/fruits.*—Seed and fruit development have not been observed on plants of the new *Senecio.*

Disease/pest resistance: Plants of the new *Senecio* have not been observed to be resistant to pathogens and pests common to *Senecio.*

Temperature tolerance: Plants of the new *Senecio* have been observed to tolerate temperatures ranging from about 0° C. to about 30° C.

It is claimed:

1. A new and distinct *Senecio* plant named 'Sunsenelibubi' as illustrated and described.

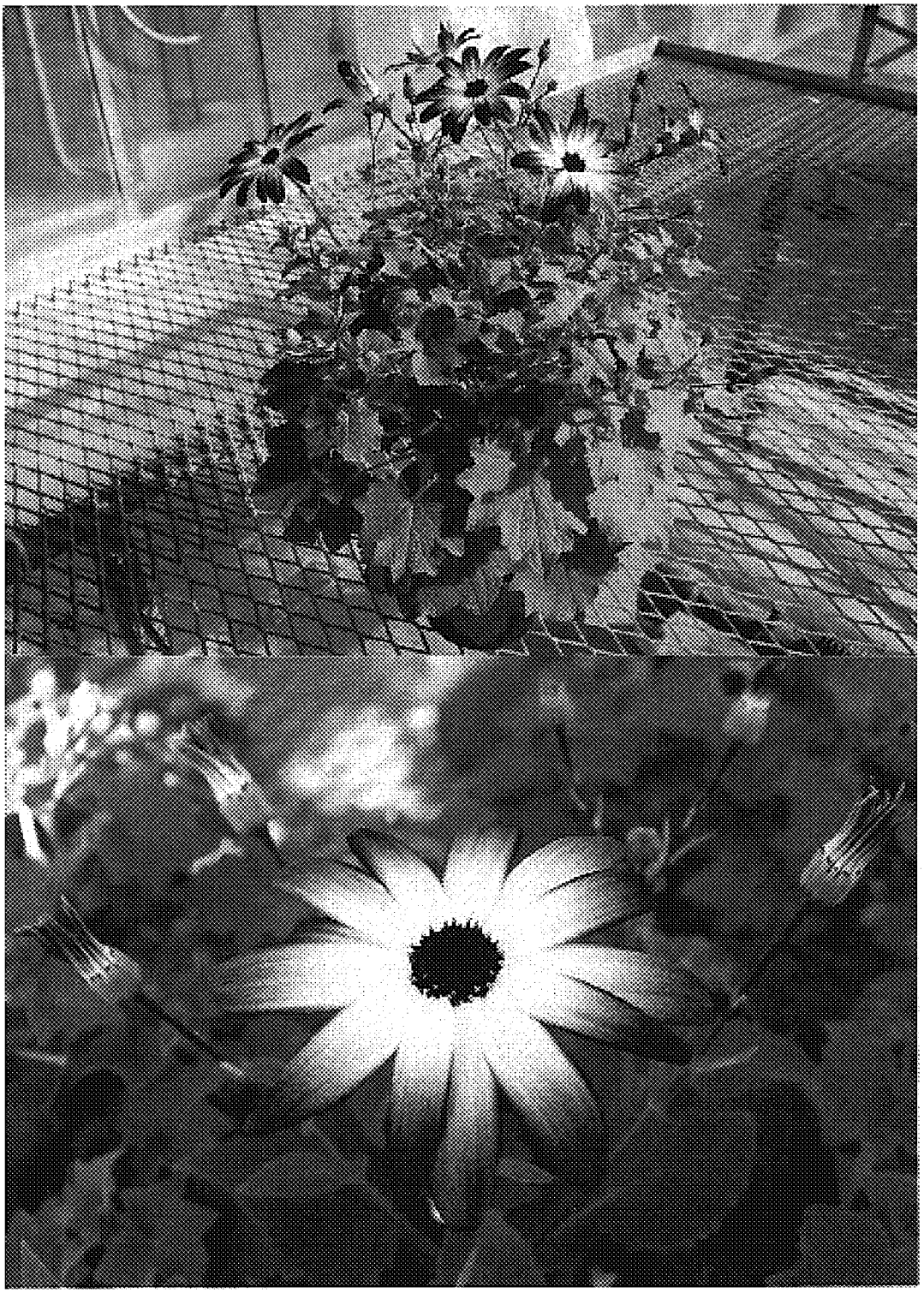

* * * * *